(12) United States Patent
Itoh

(10) Patent No.: US 7,322,525 B2
(45) Date of Patent: Jan. 29, 2008

(54) BAR-CODE READING DEVICE HAVING A MECHANISM FOR PULLING UP TEST TUBES FROM HOLDERS

(75) Inventor: Teruaki Itoh, Kumamoto (JP)

(73) Assignee: IDS Company, Ltd., Kumamoto (JP)

( * ) Notice: Subject to any disclaimer, the term of this patent is extended or adjusted under 35 U.S.C. 154(b) by 363 days.

(21) Appl. No.: 11/065,088

(22) Filed: Feb. 25, 2005

(65) Prior Publication Data

US 2005/0196323 A1 Sep. 8, 2005

(30) Foreign Application Priority Data

Mar. 8, 2004 (JP) .............................. 2004-064708

(51) Int. Cl.
*G06K 7/10* (2006.01)

(52) U.S. Cl. .......................... 235/462.43; 235/462.01; 235/475; 235/486

(58) Field of Classification Search ........... 235/462.43, 235/486, 475
See application file for complete search history.

(56) References Cited

U.S. PATENT DOCUMENTS

| 5,401,110 A | * | 3/1995 | Neeley ........................ 400/621 |
| 6,513,716 B2 | * | 2/2003 | Kitagawa ............... 235/462.43 |

FOREIGN PATENT DOCUMENTS

| JP | 09-089902 | * | 4/1997 |
| JP | 2739928 | | 1/1998 |
| JP | 2001-225820 | | 8/2001 |
| JP | 2003-294764 | | 10/2003 |

* cited by examiner

*Primary Examiner*—Seung Ho Lee
(74) *Attorney, Agent, or Firm*—Nixon & Vanderhye P.C.

(57) ABSTRACT

A bar-code reading device includes a container, a holder and a bar-code reader. The container has an outer circumferential surface on which a bar code is provided. The holder holds the container in an upright position. The bar-code reader reads the bar code from the container. A pulling mechanism pulls up the container from the holder until the bar code is completely exposed, when the bar code reader reads the bar code.

11 Claims, 3 Drawing Sheets

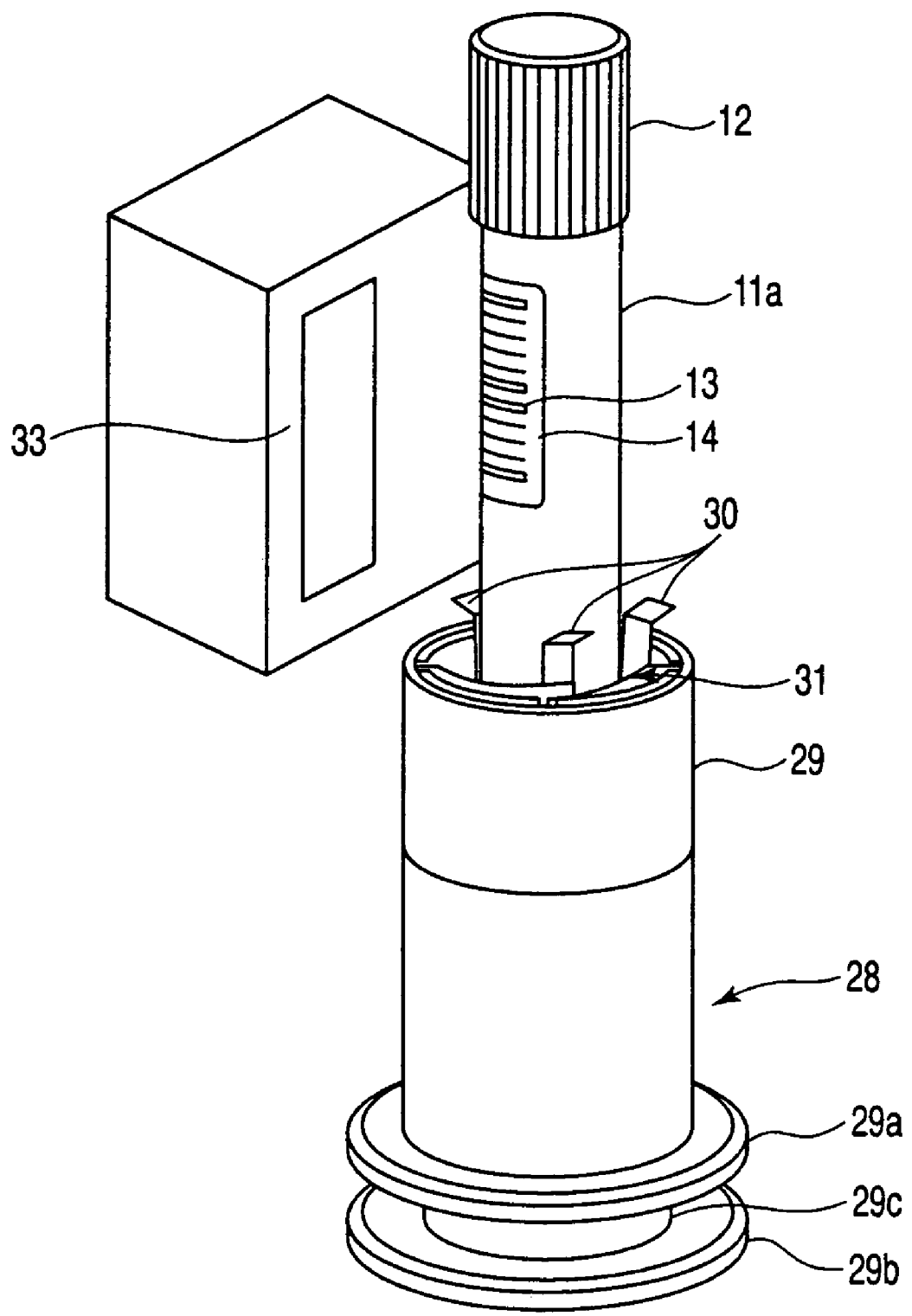
F I G. 4

BAR-CODE READING DEVICE HAVING A MECHANISM FOR PULLING UP TEST TUBES FROM HOLDERS

CROSS-REFERENCE TO RELATED APPLICATIONS

This application is based upon and claims the benefit of priority from prior Japanese Patent Application No. 2004-064708, filed Mar. 8, 2004, the entire contents of which are incorporated herein by reference.

BACKGROUND OF THE INVENTION

1. Field of the Invention

The present invention relates to a bar-code reading device for use in reading bar codes printed on, for example, the outer circumferential surface of a test tube. More particularly, the invention relates to a structure that prevents the bar code on a test tube from being concealed by the holder holding the test tube, at the time of reading the bar code from the test tube.

2. Description of the Related Art

In medical institutions such as hospitals, the blood sampled from a subject is contained in test tubes. The personal data of the subject, including the name, sex and age, and the date and time of blood sampling are printed on a bar-code label. The bar-code label is bonded to the outer circumferential surface of the test tube containing the blood sampled.

In the blood-sampling system hitherto employed in hospitals, the subjects' personal data are acquired at the reception counters. The personal data about each subject, thus acquired, is printed in the form of a bar code on a bar-code label. The bar-code label is bonded to the test tube that will contain the blood to be sampled from the subject. The test tube with the bar-code label on it is transported to the blood-sampling room of the hospital. In the blood-sampling room, the data is read from the bar-code label on the test tube. The data thus read is shown on a display. In accordance with the data displayed, the subject is called into the room. The blood is sampled from the subject. A blood-sampling system of this type is disclosed in, for example, Japanese Patent No. 2739928.

FIGS. 6 and 7 show two types of test tubes 11a and 11b, respectively. Both tubes 11a and 11b are used to contain sampled blood. The test tube 11a shown in FIG. 6 and the test tube 11b shown in FIG. 7 differ in length from each other. In other words, the test tube 11a is a short-type one and the test tube 11b is a long-type one. The test tubes 11a and 11b have an opening at the top. The opening of each tube is closed with a cap 12. Each of the test tubes 11a and 11b has a bar-code label 14 that is bonded to the outer circumferential surface of the tube. A bar code 13 is printed on the label 14, showing various data items including the date and time of blood sampling and the name of the subject.

The test tubes 11a and 11b are held in two holders 15, respectively. Each holder 15 has a holder main body 16 that is made of synthetic resin. The holder main body 16 is a hollow cylindrical member that has an opening at the upper end. Through the opening the test tube 11a or 11b can be inserted into the holder 15. The holder main body 16 has a pair of flanges 16a and 16b at the lower end. The flanges 16a and 16b are spaced in the axial direction of the holder main body 16 and arranged coaxial with each other. The holder main body 16 has a guide groove 16c. The guide groove 16c is cut in the outer surface, lying between the flanges 16a and 16b.

A guide rail 17 holds the holders 15 upright. Held in this position, the holders 15 are transported along the guide rail 17. The guide rail 17 is made of synthetic resin or metal such as aluminum alloy.

The guide rail 17 has a pair of side walls 17a and 17b. The side walls 17a and 17b extend parallel, spaced from each other by a gap. They define a transport path 17c, in which the lower parts of the holders 15 are inserted. The side walls 17a and 17b each have a guide rib 18. The guide ribs 18 extend in the lengthwise direction of the transport path 17c and protrude in the guide groove 16c of each holder main body 16. Thus, the guide ribs 18 are in sliding contact with the holder main bodies 16.

A conveyor belt 19 is arranged at the bottom of the guide rail 17. The conveyor belt 19 runs along the guide rail 17. While so running, the belt 19 contacts the bottoms of the holders 15. The holders 15 are thereby transported along the transport path 17c.

The transport path 17c has a reading position. When the holder 15 holding the test tube 11a or 11b reaches the reading position, a bar-code reader (not shown) reads the bar code 13 from the bar-code label 14 bonded to the test tube 11a or 11b.

In the conventional blood-sampling system, the holders 15 have the same size, though the test tubes 11a and 11b differ in length. Further, the test tubes 11a and 11b are inserted deep into the holder main bodies 16, having their lower ends in contact with the bottoms of the holder main bodies 16. Hence, the test tubes 11a and 11b would not slip out of the holders 15 while they are being transported.

While the long-type test tube 11b shown in FIG. 7 is held in the holder 15, the bar-code label 14 on this tube is located above the top of the holder 15. The bar code 13 is therefore exposed in its entirety. No problems will arise in reading the bar code by means of the bar-code reader (not shown).

In the case of the short-type test tube 11a, however, a part of the bar-code label 14 lies inside the holder main body 16. The holder main body 16 inevitably conceals this part of the label 14. The bar-code reader cannot read the bar code 13.

To read the entire bar code 13, the test tube 11a may be inserted in the holder main body 16, not so deep as illustrated in FIG. 6. If the test tube 11a is so inserted, however, the holder main body 16 can no longer firmly hold the tube 11a. The test tube 11a may rattle or may slip out of the holder 15 while it is being transported.

BRIEF SUMMARY OF THE INVENTION

An object of this invention is to provide a bar-code reading device that prevents bar codes from being concealed in holders and can therefore reliably read the bar codes.

Another object of the invention is to provide a bar-code reading device that can reliably read the bar codes provided on an outer circumferential surface of a test tube, while holding the test tube in a stabilized position.

To achieve the objects of the invention, a bar-code reading device according to the present invention comprises: a container which has an outer circumferential surface on which a bar code is provided; a holder which holds the container in an upright position; a bar-code reader which reads the bar code from the container; and a pulling mechanism which pulls up the container from the holder until the bar code is completely exposed, when the bar code reader reads the bar code.

To achieve the objects of the invention, another bar-code reading apparatus according to this invention comprises: a test tube having an outer circumferential surface on which a bar code is provided; a holder which holds the test tube in an upright position; a transport path which transports the holder holding the test tube and which has a reading position at a middle part; a bar-code reader which is provided at the reading position and which reads the bar code from the test tube; a tube-pulling mechanism which pulls up the test tube from the holder until the bar code is completely exposed, when the test tube is transported to the reading position; and a rotation mechanism which rotates the test tube pulled from the holder, in a circumferential direction, causing the bar code to face the bar-code reader when the bar code reader reads the bar code.

According to this invention, the bar code on the outer circumferential surface of the container (test tube) is not concealed when it is read. The bar code can therefore be reliably read.

The container is pulled from the holder only when the bar code is read from it. The container is held steadfast in the holder, all the time it is transported. The container 11a is therefore prevented from rattling or slipping out of the holder.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 4 is a perspective view representing the positional relation between the bar-code reader and a test tube held by a holder, in the embodiment of the present invention;

DETAILED DESCRIPTION OF THE INVENTION

Figure 1:
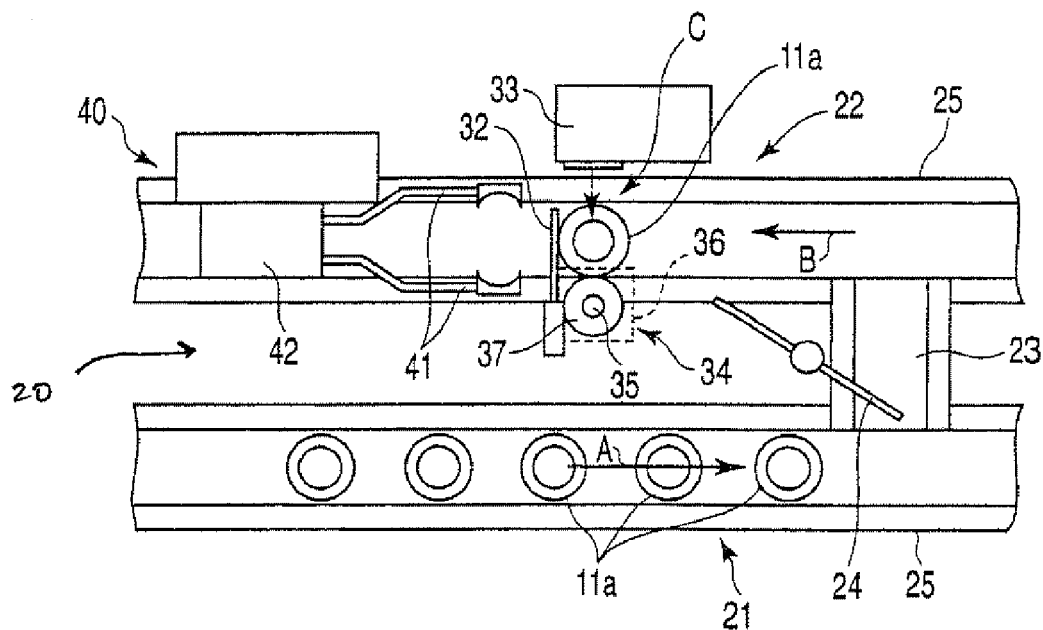
FIG. 1 is a plan view of a bar-code reading device according to an embodiment of this invention.

An embodiment of this invention will be described, with reference to FIGS. 1 to 5.

The embodiment is designed to read bar codes from test tubes 11a, each being, for example, a short-type one that contains blood. Each test tube 11a has a bar-code label 14, on which a bar code 13 printed. The bar code 13 and the bar-code label 14 are identical to those used in the conventional blood-sampling system described above. The bar-code label 14 is bonded to the outer circumferential surface of the test tube 11a.

The test tubes 11a are held by holders 28; each tube is held by one holder. They are transported, one by one, to a bar-code reading device 20 of the type shown in FIG. 1. Each holder 28 has a holder main body 29 that is made of synthetic resin. The holder main body 29 has a cylindrical hollow 31, in which the lower end part of a test tube 11a is inserted. A plurality of leaf springs 30 are laid in the hollow 31. The leaf springs 30 resiliently clamp the lower end part of the test tube 11a, holding the test tube 11a in an upright position.

Figure 2:
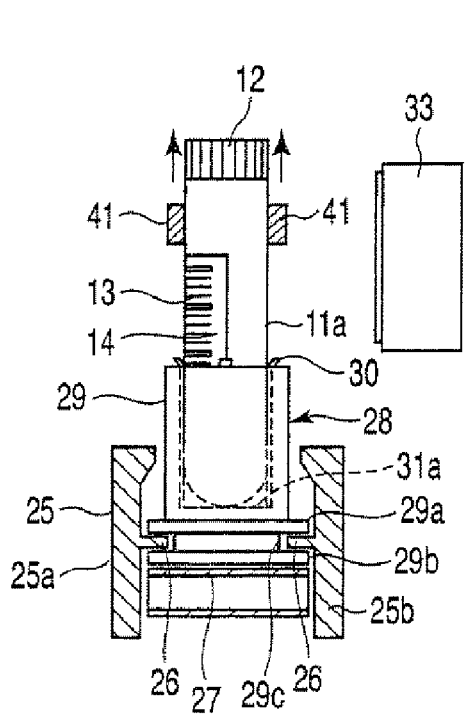
FIG. 2 is a sectional view of the bar-code reading device according to the embodiment of the invention, showing the positional relation between the bar-code reader and a test tube held by a holder.

As FIG. 2 shows, the hollow 31 of the holder main body 29 has a bottom 31a. The test tube 11a is inserted deep into the holder main body 29 until its lower end contacts the bottom 31a of the hollow 31. So inserted, the test tube 11a has a long part held in the holder 28. Hence, the test tube 11a maintains a stabilized position.

While the test tube 11a remains inserted in the holder 28, the lower part of the bar-code label 14 on the outer circumferential surface of the test tube 11a lies in the hollow 31 of the holder main body 29. Inevitably, a part of the bar code 13 is concealed in the holder 28.

Figure 3:
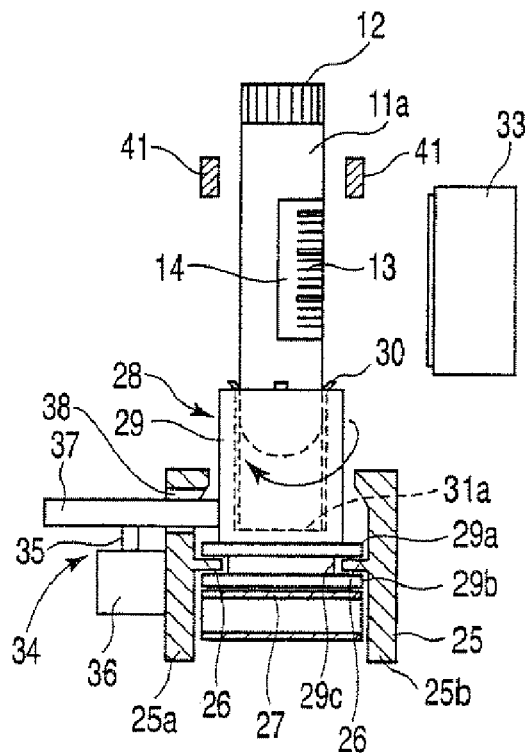
FIG. 3 is a sectional view of the bar-code reading device according to the embodiment of the invention, depicting a test tube held by a holder, pulled up and rotated to oppose the bar code on the tube to the bar-code reader.

As FIGS. 2 to 4 depict, the holder main body 29 has a pair of flanges 29a and 29b at the lower end. The flanges 29a and 29b are spaced in the axial direction of the holder main body 29 and arranged coaxial with each other. The holder main body 29 has a guide groove 29c. The guide groove 29c is an annular groove that is cut in the outer surface of the holder main body 29 and lies between the flanges 29a and 29b.

The bar-code reading device 20 is provided to read bar codes 13 from the bar-code labels 14 bonded to the test tubes 11a. As FIG. 1 shows, the bar-code reading device 20 has a first transport path 21, a second transport path 22, and a transfer path 23. The first transport path 21 and the second transport path 22 extend parallel, spaced apart from. each other. The first transport path 21 is configured to transport the holders 28, each holding a test tube 11a, in the direction of arrow A. The second transport path 22 is configured to transport the holders 28, each holding a test tube 11a, in the direction of arrow B. The transfer path 23 connects the first transport path 21 and the second transport path 22. A direction-changing lever 24 is provided at the transfer path 23.

The first and second transport paths 21 and 22 each have a guide rail 25 and a conveyor belt 27. The guide rail 25 is made of, for example, synthetic resin or metal. The guide rail 25 has a pair of side walls 25a and 25b. The side walls 25a and 25b extend parallel, spaced from each other by a gap. They each have an inner surface. The inner surfaces of the side walls 25a and 25b are opposed to each other. The side walls 25a and 25b each have a guide rib 26, on the inner surface. The guide ribs 26 extend in the lengthwise direction of the transport paths 21 and 22 and are in sliding contact with the guide grooves 29c of the holder main bodies 29. Thus, the guide rail 25 holds the holders 28 so that the hollow 31 of any holder main body 29 remains in an upright position.

In each transport path, the conveyor belt 27 lies between the side walls 25a and 25b. The conveyor belt 27 of the first transport path 21 runs along the guide rail 25, in the direction of arrow A (FIG. 1). The conveyor belt 27 of the second transport path 22 runs along the guide rail 25, in the direction of arrow B (FIG. 1). Each holder 28 held in either guide rail 25 contacts the conveyor belt 27, at the bottom of its holder main body 29. By virtue of this contact, the holder 28 holding a test tube 11a is transported along the guide rail 25.

Each holder 28 holding a test tube 11a is transported along the first transport path 21 in the direction of arrow A. The direction-changing bar 24 guides the holder 28 from the first transport path 21 to the transfer path 23. The holder 28 is then guided to from the transfer path 23 to the second transport path 22. The holder 28 is further transported along the second transport path 22 in the direction of arrow B.

As illustrated in FIG. 1, the second transport path 22 has a reading position C at its middle part. At the reading position C, there are provided a sensor (not shown) and a stopper 32. The sensor is a device for detecting whether a holder 28 holding a test tube 11a has reached the reading position C. When any holder 28 holding a test tube 11a reaches the reading position C, the sensor generates a signal, which is supplied to the stopper 32. Upon receiving the signal, the stopper 32 protrudes into the second transport path 22, temporarily stopping the holder 28 at the reading position C.

At the reading position C, a bar-code reader 33 and a rotation mechanism 34 are provided. The bar-code reader 33 is used to read the bar code 13 from the bar-code label 14 bonded to the test tube 11a at the reading position C. As FIGS. 1 to 3 show, the bar-code reader 33 lies on one side of the second transport path 22. It faces the outer circumferential surface of the test tube 11a held by the holder 28 at the reading position C.

As FIG. 3 depicts, the rotation mechanism 34 lies on the other side of the second transport path 22. It is thus opposed to the bar-code reader 33 across the second transport path 22. The rotation mechanism 34 comprises an electric motor 36 and a friction roller 37 such as a rubber roller. The motor 36 has a shaft 35 that extends vertically. The friction roller 37 is secured to the top end of the shaft 36. The outer circumferential surface of the friction roller 37 is exposed in part, to the second transport path 22 through an opening 38 cut in the side wall 25a. The friction roller 37 contacts the outer circumferential surface of the holder 28 that is stopped at the reading position C. Driven by the motor 36, the fiction roller 37 rotates the holder 28. The test tube 11a held by the holder 28 is therefore rotated, and the bar-code label 14 on the test tube 11a is positioned facing the bar-code reader 33.

As shown in FIG. 1, a tube-pulling mechanism 40 is provided near the reading position C. The tube-pulling mechanism 40 is configured to pull the test tube 11a from the holder 28 that stays at the reading position C.

Figure 5:
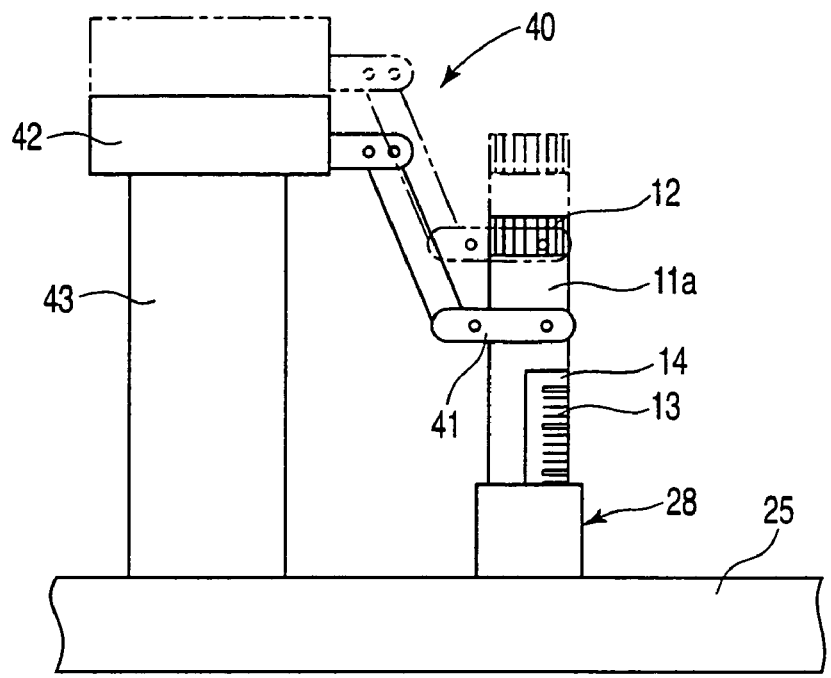
FIG. 5 is a side view of the tube-pulling mechanism of the embodiment of this invention, which is designed to pull up test tubes held by holders.
Figure 6:
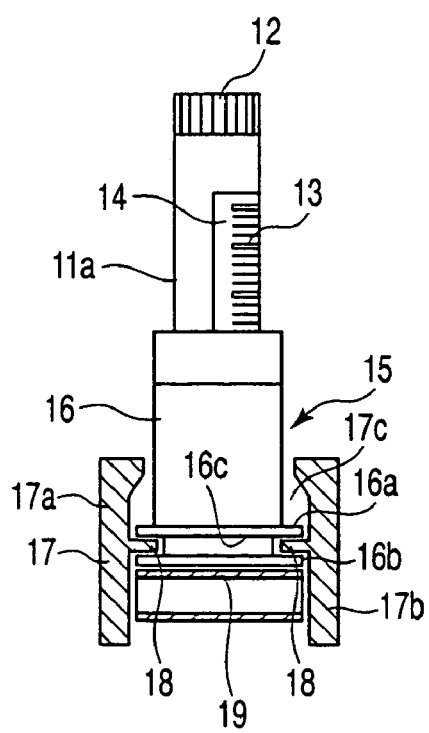
FIG. 6 is a sectional view illustrating a short-type test tube held by a holder in a conventional blood-sampling system.
Figure 7:
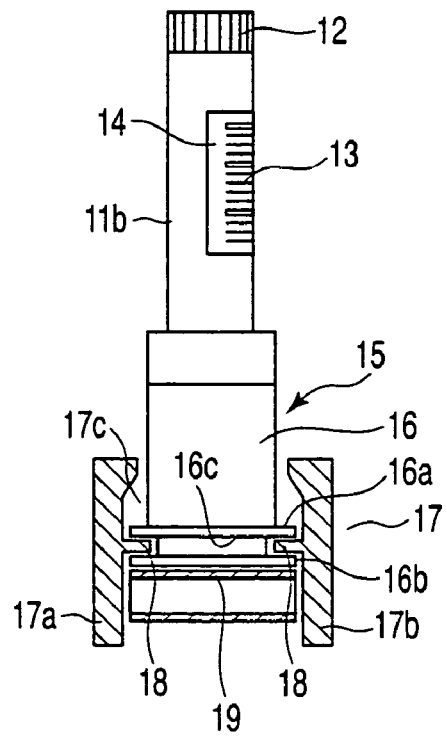
FIG. 7 is a sectional view showing a long-type test tube held by a holder in the conventional blood-sampling system.

The tube-pulling mechanism 40 has a pair of pinch arms 41, a drive unit 42 such as an air cylinder, and an elevating unit 43 (FIG. 5). The pinch arms 41 are provided to clamp the test tube 11a, at a part other than the part to which the bar-code label 14 is bonded. The pinch arms 41 can be rotated toward and away from each other. The drive unit 42 is designed to rotate the pinch arms 41 and is supported by the elevating unit 43. The elevating unit 43 can move the drive unit 42 and, hence, both pinch arms 41 up and down. The drive unit 42 and elevating unit 43 are located downstream of the reading position C, with respect to the direction of transporting the test tube 11a.

How the bar-code reading device 20 operates will be described.

Held by a holder 28, each test tube 11a containing blood stands upright. The holder 28 holding the test tube 11a is conveyed onto the first transport path 21. The conveyor belt 27 of the first transport path 21, which is running, transports the holder 28 in the direction of arrow A (FIG. 1), along the guide rail 25 of the first transport path 21. The direction-changing lever 24 guides the holder 28 from the first transport path 21 into the transfer path 23 and into the second transport path 22. In the second transport path 22, the conveyor belt 27, which is running, transports the holder 28 in the direction of arrow B (FIG. 1), along the guide rail 25.

When the holder 28 reaches the reading position C in the second transport path 22, the sensor generates a signal, which is supplied to the stopper 32. Upon receiving the signal, the stopper 32 protrudes into the second transport path 22 and temporarily stops the holder 28 at the reading position C.

Then, the drive unit 42 of the tube-pulling mechanism 40 starts operating. The pinch arms 41 are rotated toward each other until they clamp the test tube 11a that is held by the holder 28. The pinch arms 41 contact the upper end part of the tube 11a, not the part to which the bar-code label 14 is bonded.

In this state, the elevating unit 43 moves the drive unit 42 and pinch arms 41 upwards. The test tube 11a that is clamped by the pinch arms 41 is therefore pulled up from the hollow 31 of the holder 28. As a result, the entire bar-code label 14 on the test tube 11a is exposed outside the holder as is illustrated in FIG. 3.

The test tube 11a, thus pulled up, is not pulled, in its entirely, from the holder 28. As FIG. 3 depicts, its lower end part is held by the leaf springs 30. In other words, the test tube 11a is supported at two parts, i.e., the upper and lower end parts, when the elevating unit 43 moves the drive unit 42 and pinch arms 41 upwards.

Subsequently, the drive unit 42 rotates the pinch arms 41 away from each other. Hence, the pinch arms 41 no longer clamp the test tube 11a. The test tube 11a is supported by the holder 28, only at its lower end part.

The motor 36 of the rotation mechanism 34 is driven, rotating the friction roller 37. Note that the friction roller 37 contacts the outer circumferential surface of the holder 28 that is stopped at the reading position C. Therefore, the torque generated from the friction between the roller 37 and the holder 28 is transmitted from the friction roller 37 to the holder 28. The torque rotates the test tube 11a held by the holder 28, in the circumferential direction of the test tube 11a.

As the test tube 11a is so rotated, the bar-code label 14 on the test tube 11a is positioned facing the bar-code reader 33. Thus, the label 14 faces the bar-code reader 33, without fail, even if it was off the reader 33 when the test tube 11a was pulled from the hollow 31 of the holder 28. Hence, the bar-code reader 33 can reliably read the bar code 13 printed on the bar-code label 14.

When the reader 33 finishes reading the bar code 13, the motor 36 is stopped. The friction roller 37 stops rotating. Then, the drive unit 42 rotates the pinch arms 41 toward each other. The pinch arms 41 clamp the test tube 11a at the upper end part thereof. Then, the elevating unit 43 is driven, moving the drive unit 42 and pinch arms 41 downwards. The test tube 11a, which is clamped by the pinch arms 41, moves downwards until its lower end contacts the bottom 31a of the hollow 31 made in the holder 28. As a result, the test tube 11a has its lower end part held in the holder 28.

When the bar-code reader 33 finishes reading the bar code 13, the stopper 32 recedes from the second transport path 22. The holder 28 is no longer stopped at the reading position C. That is, the holder 28 is transported in the second transport path 22 to an inspection site, where the blood in the test tube 11a is inspected.

In the embodiment described above, the test tube 11a is pulled out of the hollow 31 of the holder 28, thereby exposing the entire bar-code label 14 bonded to the outer circumferential surface of the tube 11a, so that the bar code 13 may be read from the label 14. The bar code 13 would not be concealed even if the test tube 11a were a short-type one. The bar code 13 can therefore be reliably read.

Moreover, the test tube 11a remains inserted in the holder 28, with its lower end contacting the bottom 31a of the hollow 31 of the holder 28. Namely, the holder 28 holds the test tube 11a steadfast while the test tube 11a is being transported. The test tube 11a can maintain a stable position, not rattling or slipping out of the holder 28, all the time it is transported.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A bar-code reading device comprising:
   a container which has an outer circumferential surface on which a bar code is provided;
   a holder which holds the container in an upright position, the holder having a holder main body in which a lower end part of the container is inserted;
   a bar-code reader which reads the bar code from the container; and
   a pulling mechanism which pulls up the container from the holder until the bar code is completely exposed, when the bar code reader reads the bar code, the pulling mechanism being positioned to hold an upper end part of the container outside of the bar code, wherein the holder and the pulling mechanism are cooperatively disposed such that the container is supported by both the lower end part and the upper end pan when the container is pulled to completely expose the bar code.

2. The bar-code reading device according to claim 1, further comprising a rotation mechanism which rotates the container pulled from the holder, causing the bar code to face the bar-code reader when the bar code reader reads the bar code.

3. The bar-code reading device according to claim 2, further comprising a transport path which transports the holder holding the container and which has, at a middle part, a reading position, at which the bar-code reader, the rotation mechanism and the pulling mechanism are provided.

4. The bar-code reading device according to claim 1, wherein the container is a test tube which contains a sample, and the bar code represents information about the sample.

5. A bar-code reading device comprising:
   a test tube having an outer circumferential surface on which a bar code is provided;
   a holder which holds the test tube in an upright position, the holder having a holder main body in which a lower end pan of the test tube is inserted;
   a transport path which transports the holder holding the test tube and which has a reading position at a middle part;
   a bar-code reader which is provided at the reading position and which reads the bar code from the test tube;
   a tube-pulling mechanism which pulls up the test tube from the holder until the bar code is completely exposed, when the test tube is transported to the reading position, the tube-pulling mechanism being positioned to hold an upper end part of the test tube outside of the bar code, wherein the holder and the tube-pulling mechanism are cooperatively disposed such that the test tube is supported by both the lower end part and the upper end part when the test tube is pulled to completely expose the bar code; and
   a rotation mechanism which rotates the test tube pulled from the holder, in a circumferential direction, causing the bar code to face the bar-code reader when the bar code reader reads the bar code.

6. The bar-code reading device according to claim 5, wherein the holder has a plurality of leaf springs which resiliently clamp the lower end part of the test tube, and the rotation mechanism rotates both the test tube and the holder.

7. The bar-code reading device according to claim 5, wherein the tube-pulling mechanism pushes the test tube back toward the holder after the bar-code reader finishes reading the bar code.

8. The bar-code reading device according to claim 5, wherein the rotation mechanism has a friction roller and a motor which rotates the friction roller, and the friction roller transmits to the holder a torque generated from friction between the friction roller and an outer circumferential surface of the holder.

9. The bar-code reading device according to claim 5, wherein the rotation mechanism and the tube-pulling mechanism are provided at the reading position.

10. The bar-code reading device according to claim 5, wherein the transport path has a stopper which temporarily stops the holder when the holder holding the test tube reaches the reading position.

11. The bar-code reading device according to claim 5, wherein the test tube contains a sample, and the bar code represents information about the sample.

* * * * *